(12) United States Patent
Sierra et al.

(10) Patent No.: US 7,427,289 B2
(45) Date of Patent: Sep. 23, 2008

(54) MULTIPLE WAVELENGTH LASER WORKSTATION

(75) Inventors: Rafael Armando Sierra, Palmer, MA (US); Eric Calvin Koschmann, Hudson, NH (US); Joseph M. Day, Warren, MA (US); Evan Andrew Sherr, Ashland, MA (US); James Henry Boll, Newton, MA (US)

(73) Assignee: Cynosure, Inc., Chelmsford, MA (US)

( * ) Notice: Subject to any disclaimer, the term of this patent is extended or adjusted under 35 U.S.C. 154(b) by 0 days.

(21) Appl. No.: 11/035,680

(22) Filed: Jan. 14, 2005

(65) Prior Publication Data
US 2006/0161142 A1   Jul. 20, 2006

(51) Int. Cl.
*A61N 5/067* (2006.01)
(52) U.S. Cl. .............................. 607/89; 128/898; 606/9
(58) Field of Classification Search .................. 128/898; 606/9; 607/89
See application file for complete search history.

(56) References Cited

U.S. PATENT DOCUMENTS

| | | | |
|---|---|---|---|
| 3,243,650 A * | 3/1966 | Hawkins et al. ............. 315/160 |
| 3,284,665 A * | 11/1966 | Goncz ........................ 315/168 |
| 3,465,203 A * | 9/1969 | Michaels et al. ............. 315/173 |
| 3,524,144 A * | 8/1970 | Buser et al. .................... 372/70 |
| 3,651,425 A * | 3/1972 | McKnight .................... 372/70 |
| 3,725,733 A * | 4/1973 | Mack et al. .................. 315/228 |
| 4,037,136 A * | 7/1977 | Hoene ..................... 315/241 P |
| 4,065,370 A * | 12/1977 | Noble et al. ................. 427/526 |
| 4,488,104 A * | 12/1984 | Suzuki ........................ 320/166 |
| 4,910,438 A * | 3/1990 | Farnsworth .............. 315/241 P |
| 5,249,192 A * | 9/1993 | Kuizenga et al. .............. 372/23 |
| 5,331,649 A * | 7/1994 | Dacquay et al. ............... 372/23 |
| 5,507,739 A * | 4/1996 | Vassiliadis et al. .............. 606/3 |
| 5,540,676 A | 7/1996 | Freiberg .......................... 606/3 |
| 5,557,625 A | 9/1996 | Durville ....................... 372/29 |
| 5,624,435 A | 4/1997 | Furumoto et al. ............. 606/10 |
| 5,662,644 A | 9/1997 | Swor ............................. 606/9 |
| 5,746,735 A | 5/1998 | Furumoto et al. .............. 606/9 |
| 5,818,580 A * | 10/1998 | Murnick ..................... 356/311 |
| 5,843,072 A | 12/1998 | Furumoto et al. .............. 606/9 |
| 5,871,479 A * | 2/1999 | Furumoto et al. .............. 606/9 |
| 6,077,294 A | 6/2000 | Cho et al. ..................... 607/89 |

(Continued)

FOREIGN PATENT DOCUMENTS

DE      88 07 746      11/1988

(Continued)

OTHER PUBLICATIONS

English abstract of DE 88 07 746.

(Continued)

*Primary Examiner*—Henry M Johnson, III
(74) *Attorney, Agent, or Firm*—Foley & Lardner; John M Garvey

(57) ABSTRACT

Lasers capable of lasing at at least two wavelengths are provided having a lasing medium which is capable of lasing at a first wavelength and at a second wavelength. Also disclosed are laser workstations having two lasers driven by a single electronics drive system in which a single energy storage network is connected to a first laser pump chamber operative to excite a first laser medium and connected to a second laser pump chamber operative to excite a second laser medium.

38 Claims, 6 Drawing Sheets

U.S. PATENT DOCUMENTS

| | | | |
|---|---|---|---|
| 6,273,883 B1 | 8/2001 | Furumoto | 606/9 |
| 6,398,801 B1 * | 6/2002 | Clement et al. | 607/89 |
| 6,610,052 B2 | 8/2003 | Furumoto | 606/9 |
| 6,613,040 B2 | 9/2003 | Tankovich et al. | 606/3 |
| 6,613,042 B1 | 9/2003 | Tankovich et al. | 606/10 |
| 6,692,517 B2 | 2/2004 | Cho et al. | 607/88 |
| 7,118,562 B2 * | 10/2006 | Furumoto | 606/9 |
| 2002/0002367 A1 * | 1/2002 | Tankovich et al. | 606/3 |
| 2004/0105611 A1 * | 6/2004 | Bischel et al. | 385/14 |
| 2004/0225339 A1 * | 11/2004 | Yaroslavsky et al. | 607/88 |
| 2005/0015077 A1 * | 1/2005 | Kuklin et al. | 606/9 |

FOREIGN PATENT DOCUMENTS

| | | | |
|---|---|---|---|
| JP | 2001-196665 | * | 7/2001 |
| WO | WO 90/12548 | | 11/1990 |
| WO | WO 93/21843 | | 11/1993 |
| WO | WO 97/37602 | | 10/1997 |
| WO | WO 03/103529 | | 12/2003 |

OTHER PUBLICATIONS

English abstract of WO 03/103529.

* cited by examiner

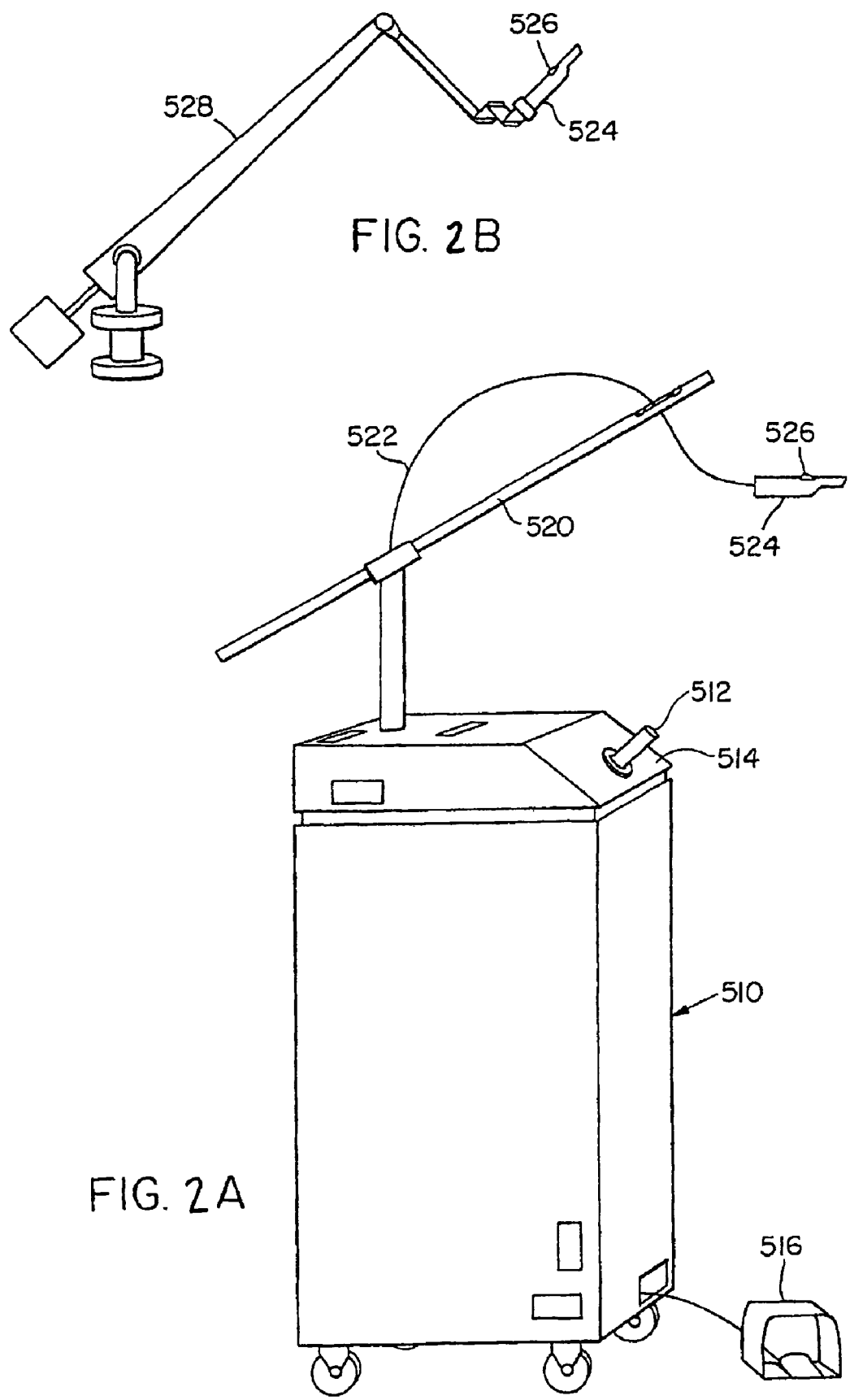

MULTIPLE WAVELENGTH LASER WORKSTATION

FIELD OF THE INVENTION

The invention relates to the field of lasers, particularly to lasers utilized in the treatment of skin and skin conditions.

BACKGROUND OF THE INVENTION

The use of electromagnetic radiation in the visible and infrared regions of the spectrum has become commonplace in many areas of industry, medicine and research. For example, such radiation is of growing importance in the field of dermatology. In many cases, laser sources are used to generate the desired radiation level at the needed wavelength.

There are a myriad of lasers that are commonly used for dermatological applications such as treatment of vascular lesions or pigmented lesions, hair removal and skin resurfacing. The principle of selective photothermolysis underlies many laser therapies and is used to treat such diverse conditions such as varicose veins, portwine stain birthmarks, other ecstatic vascular lesions, and pigmented lesions including tattoos. The dermal and epidermal layers containing the targeted structures are irradiated with light, usually from lasers or flashlamps. The wavelength of this light is chosen so that its energy will be preferentially or selectively absorbed in the structures. This creates localized heating with the intent of raising the temperature to a point at which constituent proteins will denature or pigment particles will disperse.

Recently, the treatment of aged skin has become an important aspect of cosmetic dermatology. This treatment, often referred to as "skin rejuvenation," includes elements of many of the commonly performed treatments. The goal of skin rejuvenation is to improve the appearance of aged skin by, for example, improving skin pigmentation, removing facial vessels, reducing wrinkles and fine lines, and improving skin elasticity and texture. Although numerous single-laser techniques have been proposed, there is a growing consensus that skin rejuvenation is best addressed by using multiple laser modalities. It follows that a single laser workstation that provides multiple lasers to address all of the components of skin rejuvenation would be desirable.

Presently, there are three lasers that have been shown to be particularly useful in the treatment of aged skin. These are the pulse dye laser (PDL), operating at a wavelength in the range of 585-600 nm; the Nd:YAG laser operating at 1064 nm; and the Nd:YAG laser operating at 1320 nm. The PDL improves pigmentation, can treat small facial vessels and promotes collagen stimulation. The results, particularly on fine lines and wrinkles, however, are often only subtle. The 1064 nm Nd:YAG laser can treat larger vessels and stimulate collagen, but does not have an acceptable effect on pigmentation. Finally, the 1320 nm Nd:YAG laser improves skin elasticity and reduces wrinkles and fine lines.

Generally, dermatological treatments utilizing multiple wavelengths involve separate laser systems having separate controls and separate delivery devices. An exposure is made using one laser, and subsequently the same area is exposed with a second laser. With such a method, the timing between the laser pulses is difficult to control exactly, and the time between pulses is usually seconds, rather than fractions of a second. Such timing problems may affect the clinical outcome.

A work station that included all three of these lasers would allow the practitioner to achieve optimal results in all aspects of treatment. Such a work station that merely packaged one of each of these lasers together would not be commercially attractive, however, as it would offer little to no cost advantage over three individual lasers.

It is an object of the present invention to provide a laser workstation that reduces or wholly overcomes some or all of the difficulties inherent in prior known devices. It is a further object of the invention to provide a laser workstation that provides laser output at 585-600 nm, 1064 nm and 1320 nm. Particular objects and advantages of the invention will be apparent to those skilled in the art, that is, those who are knowledgeable or experienced in this field of technology, in view of the following disclosure of the invention and detailed description of certain preferred embodiments.

SUMMARY

In accordance with a first aspect, lasers capable of lasing at at least two wavelengths are provided. The laser has a lasing medium which is capable of lasing at a first wavelength and at a second wavelength. In certain embodiments, the lasing medium is capable of lasing at the first and second wavelengths each to a sufficient degree to produce laser output of sufficient power for the intended purpose(s) to which the laser is being applied. The lasing medium has a longitudinal axis, along which an output coupler resides at a first end of the lasing medium. At a second end of the lasing medium, a first mirror and a second mirror are located along the longitudinal axis, the second mirror being located between the first mirror and the lasing medium. The first mirror is highly reflective at a first wavelength, and the second mirror is highly reflective at a second wavelength while being transparent at the first wavelength. A beam block shutter is arranged to be movable between a first position along the longitudinal axis of the lasing medium and between the first and second mirrors and a second position away from the longitudinal axis of the lasing medium.

Under operation, the second mirror reflects radiation at the second wavelength while allowing radiation at the first wavelength to pass through it. When the beam block shutter is in the first position, along the light path of the lasing medium, the beam block shutter prohibits radiation that passes through the second mirror from reaching the first mirror and being reflected back into the lasing medium. Thus, only radiation at the second wavelength is reflected, amplified and ultimately emitted. When the beam block shutter is in the second position, out of the longitudinal axis of the lasing medium and thus out of the light path, radiation at the first wavelength passes through the second mirror to the first mirror and is reflected back into the lasing medium. Simultaneously, radiation at the second wavelength is reflected back into the lasing medium. The output coupler is selected to permit the emittance of radiation at either or both of the first and second wavelengths. Such an arrangement advantageously permits the laser resonator to have all of the critical optical components (the lasing medium, the mirrors and the output coupler) mounted in a stationary fashion rather than requiring a tuning element or switching of mirrors, resulting in a robust and relatively maintenance-free workstation, capable of emitting two wavelengths from a single lasing medium.

In accordance with a second aspect, laser workstations are provided having two lasers and a single electronics drive system. The single energy drive system is operatively connected by a switch to a first laser pump chamber that excites a first lasing medium and to a second laser pump chamber that excites a second lasing medium. In certain embodiments, the laser pump chambers are each connected to the single energy storage network by high voltage trigger transformers, secondary windings of which are in series with excitation sources within the pump chambers, for example, lamps such as flashlamps, and thus are inductors in the excitation source discharge circuits. These high voltage trigger transformers are each operative to ionize the excitation sources in the pump chambers. Upon closing the switch, stored energy from the single energy drive system flows into whichever excitation source has been ionized and causes the laser associated with that lamp to discharge its energy.

In certain embodiments, one or more of the lasers comprises a laser capable of lasing at at least two wavelengths in accordance with the first aspects described above. In certain embodiments, the laser workstation comprises a pulse dye laser (PDL) and an Nd:YAG laser. The pulse dye laser in certain embodiments has an output of 575-650 nm, for example about 585 nm. The Nd:YAG laser comprises an Nd:YAG laser resonator having an Nd:YAG lasing medium with a longitudinal axis along which laser energy is emitted. An output coupler is located at a first end of the Nd:YAG lasing medium along the longitudinal axis of the Nd:YAG lasing medium. A first mirror is located along the longitudinal axis of the Nd:YAG lasing medium at a second end of the lasing medium, and a second mirror is located along the longitudinal axis of the Nd:YAG lasing medium between the first mirror and the lasing medium. The first mirror is highly reflective at at least 1064 nm. The second mirror is highly reflective at 1320 nm and is substantially transparent at 1064 nm. The second mirror in certain embodiments is treated to be substantially transparent at 1064 nm, for example, by being coated with a coating that is anti-reflective at 1064 nm. The Nd:YAG laser resonator further comprises a beam block shutter that is opaque and nonreflective. The beam block shutter is movable from a first position along a longitudinal axis of the Nd:YAG lasing medium between the first and second mirrors to a second position away from the longitudinal axis of the Nd:YAG lasing medium. The Nd:YAG lasing medium emits at both 1064 nm and at 1320 nm. Such an arrangement advantageously permits the laser resonator to have all of the critical optical components (the lasing medium, the mirrors and the output coupler) mounted in a stationary fashion rather than requiring a tuning element or switching of mirrors, resulting in a robust and relatively maintenance-free workstation.

Under operation, the second mirror reflects the 1320 nm radiation while permitting the 1064 nm radiation to pass. When the beam block shutter is in the first position, along the light path of the lasing medium, the beam block shutter prohibits the 1064 nm radiation that passes through the second mirror from reaching the first mirror and being reflected back into the lasing medium. Thus, only the 1320 nm radiation is reflected, amplified and ultimately emitted. When the beam block shutter is in the second position, out of the longitudinal axis of the lasing medium and thus out of the light path, the 1064 nm radiation passes through the second mirror to the first mirror and is reflected back into the lasing medium. The Nd:YAG lasing medium has a stimulated emission cross-section at 1064 nm that is much greater than the stimulated emission cross-section at 1320 nm. Accordingly, an output coupler can be selected such that the laser operates at 1064 nm.

In accordance with another aspect, laser workstations are provided having two lasers and a single electronics drive system. The single energy drive system is operatively connected by active semiconductor switches to a first laser pump chamber that excites a first lasing medium and to a second laser pump chamber that excites a second lasing medium. The active semiconductor switches allow for the selective release of portions of energy from a single energy storage network, for example, a capacitor bank, to its associated lamps and ultimately to the associated laser. The release of less than the total amount of stored energy allows for the rapid or immediate firing of either the first laser or the second laser in a series of partial-energy releases, resulting in a series of "sub-pulses" of laser energy of different wavelengths.

In certain embodiments of the various aspects described above, the laser workstation further comprises a handpiece operatively connected, for example, by means of a optical fiber or a wave guide, to the pulse dye laser and to the Nd:YAG laser. The handpiece in certain embodiments comprises a plurality of lenses operative to image the laser radiation, optionally adjustably.

Methods of treating skin problems utilizing laser systems disclosed herein are also provided. In one aspect, a laser system in accordance with the first aspect is used to apply laser energy at a first wavelength to an area of skin affected by a skin problem. The same laser system is used to apply laser energy at a second wavelength to the same area of skin. In this way, the skin problem is treated with two different wavelengths of laser energy from the same laser system, indeed from the same laser itself.

In another aspect, a laser system in accordance with those disclosed herein is used to treat skin affected by a skin problem. Laser energy from both the first laser and the second laser is applied to the area of skin affected by a skin problem. Typically, the wavelength of the laser energy from the first laser differs from the wavelength of the energy from the second laser, such that the area of skin can be treated with each of two beneficial wavelengths of laser energy of different wavelengths in a single treatment session. In certain embodiments, sub-pulses of laser energy are utilized to treat skin affected by a skin problem. Such a method has the advantage of permitting greater control over the duration of time between applications of the different wavelengths of laser energy, as well as permitting the two wavelengths to be applied in a much shorter period of time, perhaps instantaneously. These factors may lead to improved results in the treatment of skin problems.

A more specific example of using multiple wavelength pulses to treat a skin lesion is having a 595 nm wavelength generated with a pulse dye laser and a 1064 nm wavelength generated with a solid-state laser. To eradicate a vascular lesion, a pulse of 595 nm is followed by another pulse at 1064 nm radiating at the same area of the skin lesion. The pulse at 595 nm at an effective fluence converts the oxy-hemoglobin contained in the red blood cells in the ecstatic vascular lesion to met-hemoglobin that has a much higher absorption coefficient at a 1064 nm wavelength. With the wavelength multiplexing technique mentioned, the treatment efficacy is dramatically improved. The energy or fluence required is thus dramatically reduced.

These and additional features and advantages of the invention disclosed here will be further understood from the following detailed disclosure of certain preferred embodiments.

BRIEF DESCRIPTION OF THE DRAWINGS

FIGS. 2A is an embodiment of a laser workstation;

FIG. 2B is an alternative embodiment of a portion of a laser workstation;

Figure 1:
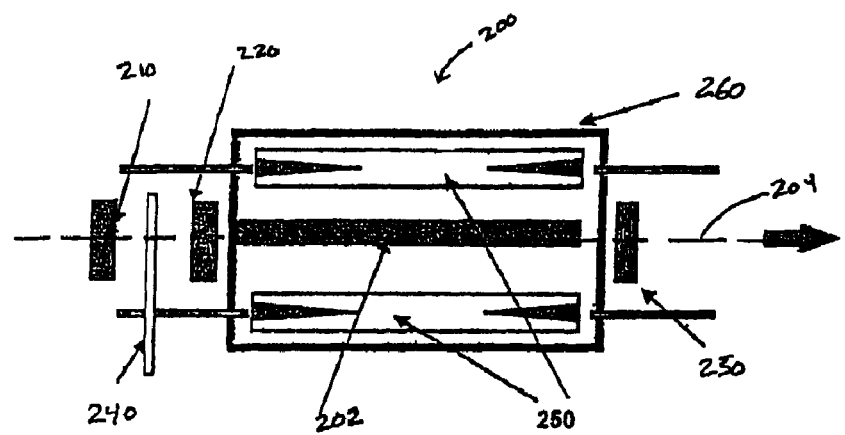
FIG. 1 is a schematic representation of an embodiment of an laser having a lasing medium capable of lasing at two wavelengths.

The figures referred to above are not drawn necessarily to scale and should be understood to present a representation of the invention, illustrative of the principles involved. Some features of the laser workstation depicted in the drawings have been enlarged or distorted relative to others to facilitate explanation and understanding. The same reference numbers are used in the drawings for similar or identical components and features shown in various alternative embodiments. Laser workstations, as disclosed herein, will have configurations and components determined, in part, by the intended application and environment in which they are used.

DETAILED DESCRIPTION OF CERTAIN EMBODIMENTS

Lasers and laser workstations in accordance with the current invention may be embodied in various forms. Certain embodiments are described in further detail below.

Figure 4A:
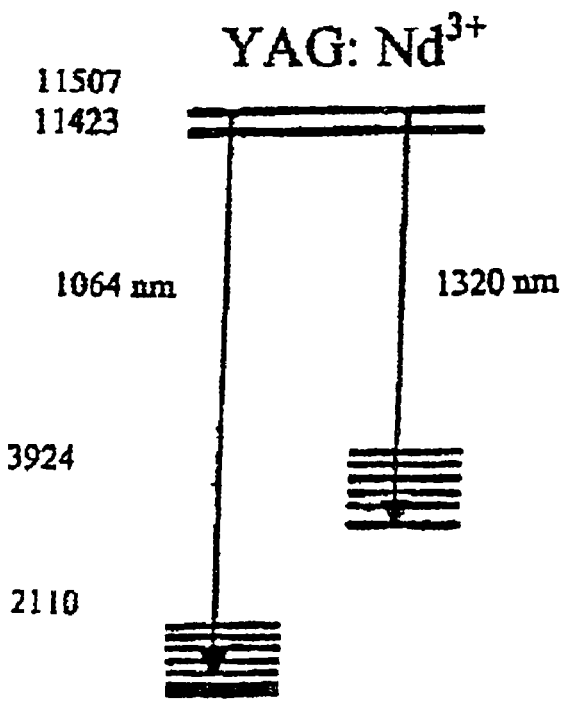
FIG. 4A is an energy level diagram for a Nd:YAG laser.

FIG. 1 shows an embodiment of a laser, here an Nd:YAG laser. The emittance at two wavelengths of the Nd:YAG laser is illustrated in the energy level diagram of FIG. 4A.

Figure 4B:
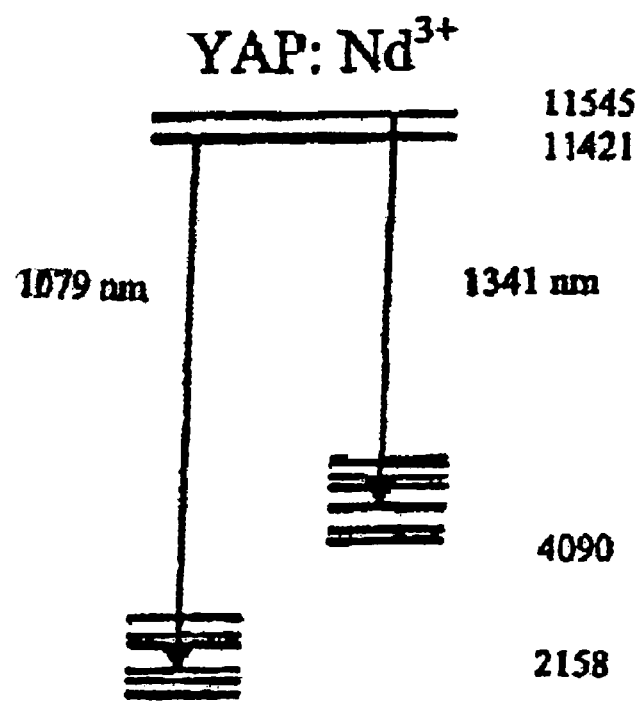
FIG. 4B is an energy level diagram for a YAP:Nd: laser.

Other suitable lasers include any laser capable of emitting at at least two wavelengths and include, for example, crystal lasing mediums, gas lasing mediums, dye lasing mediums or other types of lasing media. For example, a YAP:Nd lasing medium is capable of lasing at 1079 nm and/or at 1341 nm, as illustrated in the energy level diagram of FIG. 4B. Such a medium is described in U.S. Pat. No. 6,613,040, which is hereby incorporated herein in its entirety for all purposes. Other suitable lasing media include but are not limited to other rare earth and transition ion dopants as well as other crystal and glass hosts of these dopants. Examples of such dopants include Erbium, Chromium and Titanium. Examples of other hosts include fluoride crystals such as YLF, vanadite crystals such as YVO and fluoride glasses such as ZBLN and silicaglasses. Other suitable lasing media will be readily apparent to those of skill in the art, given the benefit of this disclosure. Referring back to FIG. 1, Nd:YAG laser resonator 200 has an Nd:YAG laser medium 202, here a crystal rod, having a longitudinal axis 204. The Nd:YAG laser resonator 200 further comprises flashlamps 250 to excite the Nd:YAG laser medium. Other suitable excitation means may be utilized, and such will be readily apparent to those skilled in the art, given the benefit of this disclosure. The Nd:YAG laser medium 202 and flashlamps 250 are contained within pump chamber 260.

The Nd:YAG resonator further comprises a first mirror 210 and a second mirror 220. The first mirror 210 is highly reflective at at least 1064 nm. For example, in certain embodiments the first mirror has a reflectance of at least 90%, for example at least 95%, optionally at least 99.5% at 1064 nm. The second mirror is highly reflective at 1320 nm and is substantially transparent at 1064 nm. Substantially transparent, as used herein, means that the mirror permits light at the given wavelength to pass through, in either direction, to a sufficient extent to permit sufficient laser output to be generated at that wavelength for the treatment of skin. In other words, the mirror must be sufficiently nonreflective, nonrefractive and nonabsorbent at said wavelength to permit sufficient laser output to be generated at that wavelength for the treatment of skin. The creation of such mirrors is known in the art, and is accomplished, for example, by coating a mirror comprised of a suitable material with a coating that is anti-reflective at 1064 nm. Commercially available dielectric coatings are commonly used in this application. Such coatings are typically made up of multiple thin layers of dielectric materials such as magnesium fluoride and heavy metal oxides. The Nd:YAG laser resonator further comprises a receptacle for an output coupler 230. The output coupler is chosen to be partially reflective to allow the lasing medium to resonate while permitting laser output. The mirrors and output coupler may be plane parallel, hemispherical or spherical. Suitable configurations for the laser resonator will be readily apparent to those skilled in the art, given the benefit of his disclosure.

The Nd:YAG laser resonator further comprises a beam block shutter 240 that is opaque and nonreflective at least at about 1064 nm. The beam block shutter is movable from a first position along longitudinal axis 204 of the Nd:YAG lasing medium between the first and second mirrors to a second position away from the longitudinal axis of the Nd:YAG lasing medium. As is illustrated in FIG. 4, the Nd:YAG lasing medium emits at both 1064 nm and at 1320 nm. The beam block shutter permits the exclusion of 1064 nm light from reaching the first mirror and thus from resonating and being emitted. With the blocker in the first position along the longitudinal axis, and thus in the light path, the Nd:YAG laser will emit only at 1320 nm. With the shutter in the second position and thus removed from the light path, both wavelengths are emitted. As the stimulated emission cross-section for operation at 1064 nm is much greater than that for operation at 1320 nm, it is a simple matter to select an output coupler such that the laser in this mode will operate at 1064 nm. The configuration of the Nd:YAG laser resonator permits the laser resonator to have all of the critical optical components (the lasing medium, the mirrors and the output coupler) mounted in a stationary fashion rather than requiring a tuning element or switching of mirrors, resulting in a robust and relatively maintenance-free workstation having three laser outputs while utilizing only two lasers.

FIG. 2A shows an embodiment of a laser workstation. The workstation comprises a main unit 510 that contains a pulse dye laser and an Nd:YAG laser. FIG. 1 shows an embodiment of an Nd:YAG laser. A calibration port 512 and a front control panel 514 are provided. Footswitch 516 is used for convenient control. A swing arm 520 holds the optical delivery fiber 522 that ends in a handpiece 524. The handpiece has a finger-switch 526 as an alternate means for activation. FIG. 2B shows an alternative embodiment that utilizes an articulated arm 528 that is appropriate for a quartz fiber delivery system. Other suitable configurations for other suitable delivery systems will be readily apparent to those of skill in the art, given the benefit of this disclosure.

The laser workstation comprises a pulse dye laser. Certain embodiments of the laser workstation include a pulse dye laser having a wavelength of between about 570 nm and 650 nm. Pulse dye lasers and methods of utilizing such in the treatment of skin are described in U.S. Pat. No. 6,077,294, which is hereby incorporated by reference in its entirety for all purposes. The pulse dye laser may in certain embodiments operate at a deep penetrating wavelength of about 585 nm, so as to target hemoglobin of blood in skin tissue. Hemoglobin absorbs this particular laser energy, with resultant generation of heat. Heat is generated in the skin up to about 1 mm to 1.2 mm in depth and typically uses energy of less than 5 Joules per square cm. In certain embodiments, the pulse dye laser has a target spot size of about 10 mm in diameter. In certain embodiments, the pulse width of the pulse dye laser has a range of 150 microseconds to about 1500 microseconds, optionally with a width of about 450 microseconds. The wavelength of the pulse dye laser lies in a range of about 570 nanometers to about 650 nanometers, for example in a range of about 585 nanometers to about 600 nanometers. In certain embodiments, the pulse dye laser operates at a wavelength of about 585 nanometers. The pulse dye laser may provide a fluence of less than 5 Joules per square cm, for example, 3 Joules per square cm at a 10-millimeter diameter skin treatment spot. By treating the skin to this low fluence pulse dye laser light, collagen may be stimulated to regenerate and "fill in" valleys of wrinkles for a younger, more clear skin.

Figure 3A:
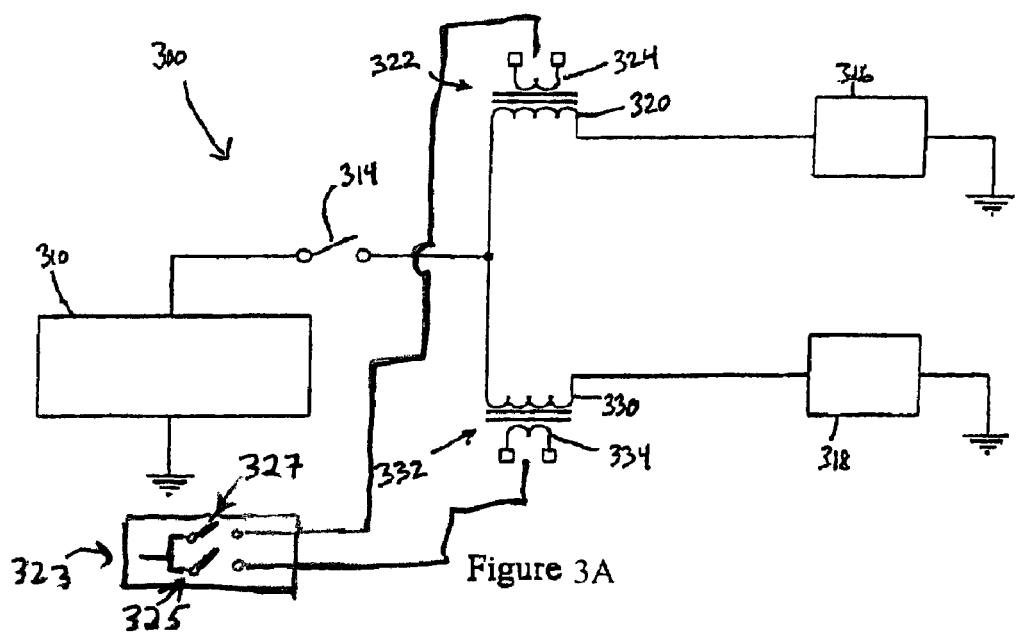
FIG. 3A is a schematic representation of an embodiment of a single electronics drive system.
Figure 3B:
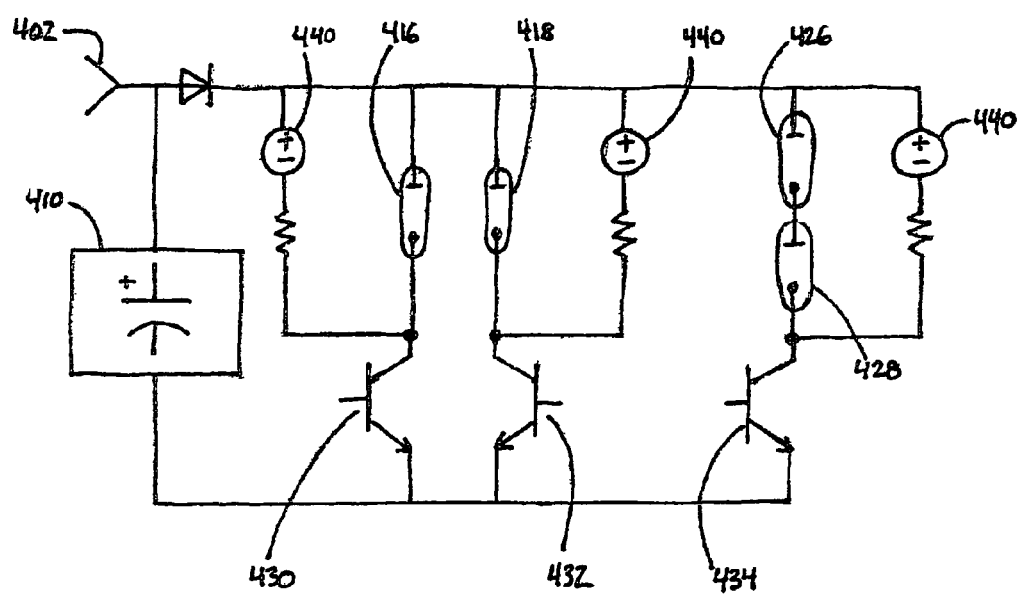
FIG. 3B is a schematic representation of another embodiment of a single electronics drive system.

FIG. 3A illustrates a single electronics drive system comprising two different lasers, here an Nd:YAG laser and a pulse dye laser. Of course, any type of laser susceptible to excitation by a suitable excitation source may be utilized in such an arrangement. Suitable lasers include those described throughout this specification and will be readily apparent to those of skill in the art, given the benefit of this disclosure. Certain embodiments may utilize as one of the lasers a laser capable of emitting at at least two wavelengths in accordance with those described above. Referring to FIG. 3, each of the lasers is excited by one or more flashlamps (not shown) that are operated by a single electronics drive system 300. A single energy storage network 310 is connected by switch 314 to Nd:YAG pump chamber 316 and to dye pump chamber 318. Switch 314 may be triggered by a foot petal, a switch connected to a handpiece, or other by means. Switch 314 is ordinarily opened. Between Nd:YAG pump chamber 316 and switch 314 is secondary winding 320 of Nd:YAG trigger transformer 322. Similarly, between dye pump chamber 318 and switch 314 is secondary winding 330 of dye trigger transformer 332. Trigger transformers 322 and 332 are high voltage trigger transformers. Each of the secondary windings of the trigger transformers are in series with flashlamps in Nd:YAG pump chamber 316 and dye pump chamber 318, respectively, and act as inductors in discharge circuits of the flashlamps. By providing a driving pulse (e.g., from controller 323) to the primary windings 324, 334 of trigger transformers 322 and 332, respectively, the lamps in either pump chamber can be ionized (e.g., by selectively closing switch 325 or switch 327, respectively). When switch 314 is then closed, energy from the energy storage network 310 will flow through the pump chamber whose lamps have been previously ionized. In this manner, a single energy storage and pulse discharge means can be used to drive either laser pump chamber, further conserving space and reducing size of the laser workstation. In other embodiments, either or both of the lasers may be excited by any known means capable of being ionized prior to discharge, for example, by optical pumping, such as, for example, using a source such as a pulsed ultraviolet source. Suitable excitation sources will be readily apparent to those skilled in the art, given the benefit of this disclosure.

The above embodiment allows the user to select the laser to be fired and to discharge the full quantity of energy stored in the energy storage network to that laser. Prior to firing the other laser, or to re-firing the laser first selected, the energy storage network must be recharged. An alternate embodiment that permits the selective discharge of portions of the stored energy to the lasers is exemplified in FIG. 3B. This embodiment comprises two different lasers, here an Nd:YAG laser and a pulse dye laser. Again, any type of laser susceptible to excitation by a suitable excitation source may be utilized in such an arrangement. Suitable lasers include those described throughout this specification, including those capable of emitting at multiple wavelengths, and will be readily apparent to those of skill in the art, given the benefit of this disclosure. High voltage power supply 402 is operably connected to capacitor bank 410 to charge one or more capacitors (not illustrated) in the capacitor bank. The capacitors serve as an energy storage system for the laser workstation. The capacitors are operably connected to flashlamps 416 and 418, which serve to pump a pulse dye laser (not illustrated), and to flashlamps 426 and 428, which serve to pump an Nd:YAG laser (not illustrated). In the embodiment illustrated herein, flashlamps 416 and 418 are arranged in parallel such that they straddle the pulse dye laser, while flashlamps 426 and 428 are arranged in series to accommodate the full length of the Nd:YAG laser crystal, which is typically longer than the pulse dye laser. Any arrangement of flashlamps in parallel or in series will be readily accomplished by one of skill in the art, given the benefit of this disclosure.

Figure 6:
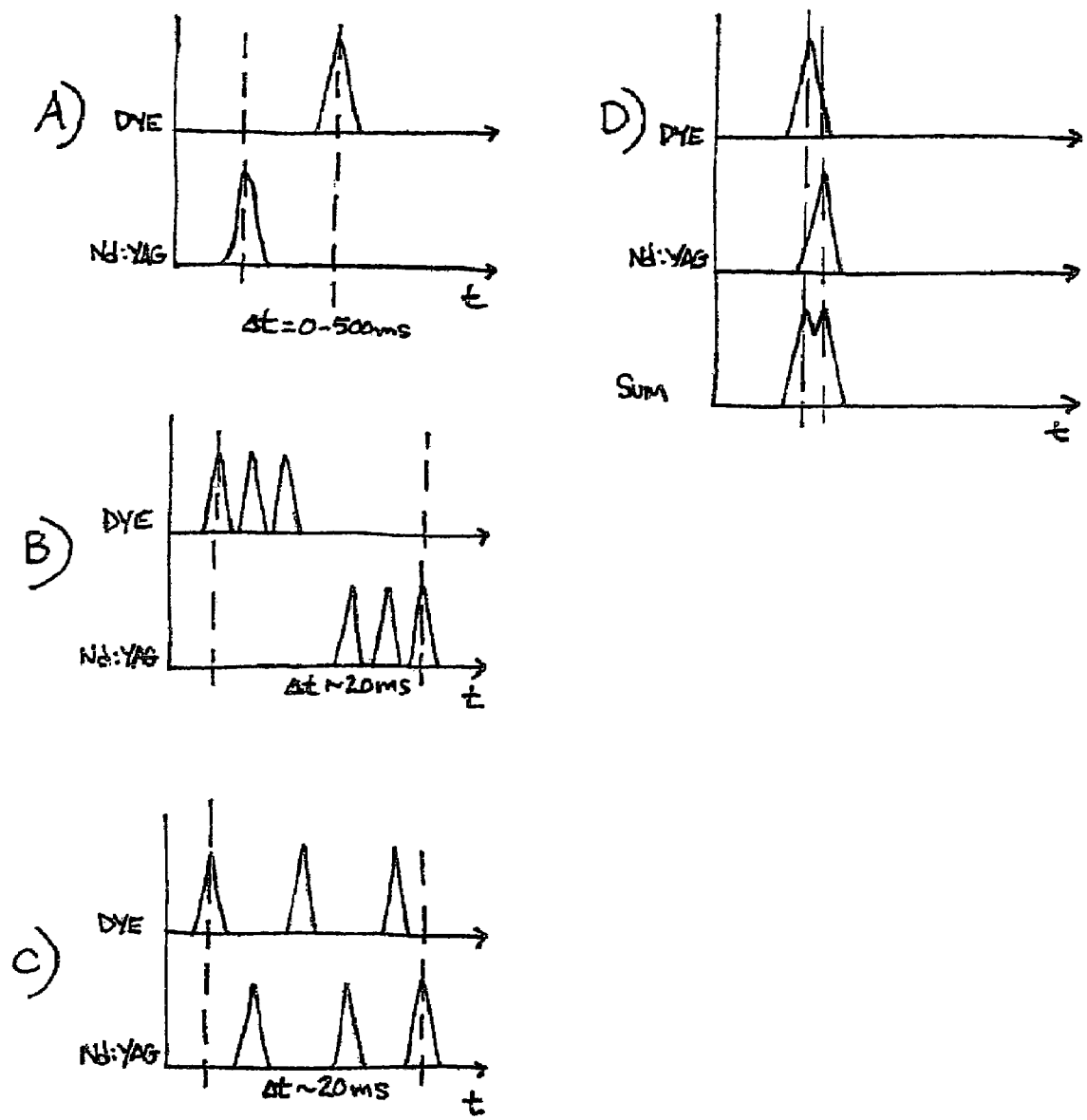
FIGS. 6A-6D are graphical representations of various sub-pulse configurations.

The capacitor bank 410 is connected to each of the flashlamps 416, 418, 426 and 428 by insulated gate bipolar transistors (IGBT's) 430, 432 and 434. In the case of flashlamps 426 and 428, which are arranged in series, a single IGBT 434 resides between the capacitor bank and the two flashlamps. While an IGBT is illustrated in this embodiment, any active semiconductor switch may be employed, for example, field effect transistors (FET's) such as MOSFET, Jfet (Junction FET) Ujt (Unijunction FET), or Darlington transistors and the like. Suitable active semiconductor switches will be readily apparent to those of skill in the art, given the benefit of this disclosure. The active semiconductor switches may be controlled by a computer, allowing for precision control over duration of time that they are closed and thus the quantity of energy that they allow to pass when closed. Such switches allow for the controlled and optionally preprogrammed completion of the circuit such that discreet quantities of energy, which may include the entirety of the energy stored in the capacitor bank or only portions of the energy stored in the capacitor bank, may be passed through to the flashlamps. When less than the entirety of the stored energy is discharged into a flashlamp, the excess of the stored energy remains to be discharged into any of the flashlamps immediately. This allows for numerous alternatives for arranging such partial pulses, or "sub-pulses," to be delivered. For example, a sub-pulse from the Nd:YAG laser could be followed by a sub-pulse from the pulse dye laser in a time from of as low as 0-500 ms, as exemplified in FIG. 6A. As another example, repeated sub-pulses of laser energy from the same laser, e.g. a "pulse train," can be achieved. For example, a pulse train from the pulse dye laser can be followed by a pulse train from the Nd:YAG laser, as illustrated in FIG. 6B, or for rapid alteration or intercalated between the two lasers, as exemplified in FIG. 6C. Optionally, both lasers may be fired simultaneously or may overlap, as exemplified by the overlapping sub-pulses of FIG. 6D. Of course, in any of these examples, either the pulse dye laser or the Nd:YAG laser could be fired first. Any such combination of sub-pulses is possible, limited only by the quantity of energy that is stored in the capacitor bank and the speed at which the IGBT operates. In the case of a laser resonator that provides the option of emitting at different wavelengths, the speed at which the resonator can switch from one wavelength to another, e.g., the time for the beam block shutter to move from one position to the next, is typically longer than the speed at which the active semiconductor switch operates and serves to limit the speed of firing at the different wavelengths. Further, depending on the duration that the active semiconductor switches are closed, a parameter which is actively controllable, the amount of energy delivered by the sub-pulses can be varied, limited ultimately by the total quantity of energy stored in the capacitor bank. Other suitable combinations will be suggested by the particular use to which the laser system is being employed, and will be readily apparent to those of skill in the art, given the benefit of this disclosure.

This system may advantageously allow for the delivery, via the sum of the sub-pulses, of a greater amount of the energy stored in the energy storage network than is achievable with a single pulse. This may result in the energy storage system taking longer to be recharged. Also, depending on the particular components used, a second sub-pulse may start at a lower voltage than the first sub-pulse. This lower voltage may enhance the discharge conditions for the Nd:YAG laser but be less suited for the pulse dye laser, meaning that better performance would be achieved by using the pulse dye laser followed by the Nd:YAG laser. Suitable components for this embodiment will be readily apparent to one of skill in the art, given the benefit of this disclosure.

Flashlamps 416, 418, 426 and 428 are ignited and maintained in a state of ionization by lamp simmer power supplies 440, which are wired in parallel with the flashlamps. In this fashion, the lamps are maintained in a state in which they can immediately be utilized in accordance with the rapid fire techniques just discussed.

Any of the above-described laser workstation embodiments may further comprises a handpiece connected critically, by an optical fiber or wave guide, to the pulse dye laser generator device and to the Nd:YAG laser generator device. The handpiece may be connected to each laser by means of a separate critical connection to each laser head, or may optionally be connected to both lasers by means of a single critical connection. The handpiece optionally focuses, through a plurality of lenses, the laser light from the laser generators onto a spot so as to stimulate skin rejuvenation. For example, the handpiece may focus laser light from the pulse dye laser onto a spot of about 10 mm in diameter to stimulate new collagen growth beneath the epidermis without injuring the surrounding structures.

Figure 5:
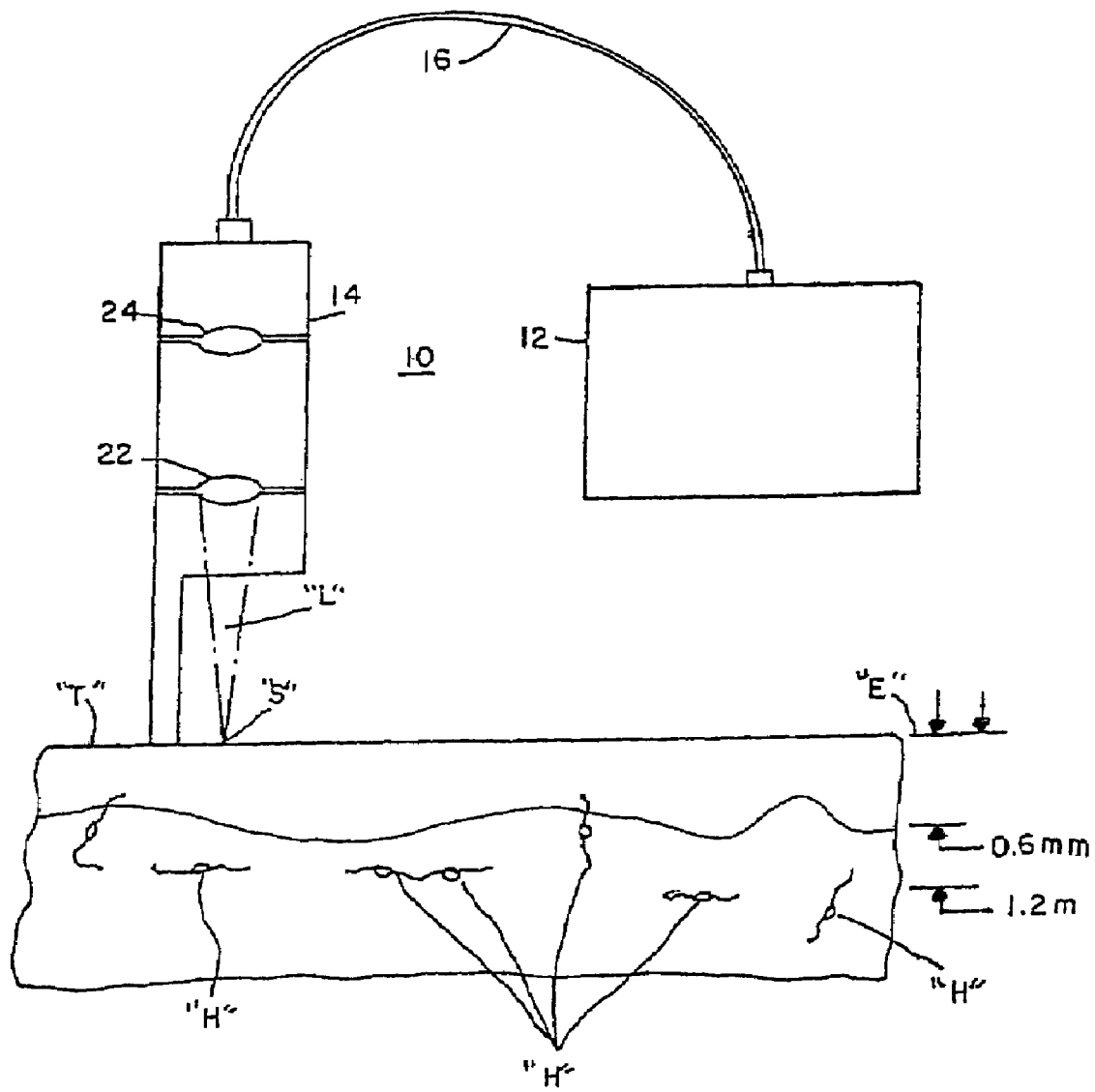
FIG. 5 is a schematic representation of an embodiment of the laser apparatus as it is applied to a layer of skin.

Laser workstations in accordance with those described herein can be utilized to treat a variety of skin conditions, including, for example, aged skin, wrinkled skin, sun-damaged skin, acne or acne-scarred skin, scars, undesirable veins such as leg or facial veins and other vascular problems. For example, a method for the treatment of wrinkles is provided in which the pulse dye laser is utilized to stimulate collagen growth beneath the epidermal layer. Such a method is exemplified in FIG. 5, which is a schematic representation of an embodiment of the laser workstation comprising laser system 10. Laser system 10 utilizes both a laser output generator 12 having both a pulse dye laser and an Nd:YAG laser for the treatment of skin. The pulse dye laser is tuned to deliver light at a wavelength of about 585 nm and a pulse width in the range of about 150 microseconds to about 1500 microseconds, for example 450 microseconds. The laser output generator 12 is operatively connected to a handpiece 14 by an optical fiber or wave guide 16. The handpiece 14 focuses, through a plurality of lenses 22 and 24, the laser light "L" onto a spot "S" of about 10 mm in diameter or larger, with a fluence typically of less than 5 Joules per square cm, to reach hemoglobin "H" of blood in a collagen layer beneath the surface of the wrinkled tissue. The laser energy is absorbed by hemoglobin "H," resulting in heat being generated in the skin tissue "T" in an area of up to about 1 mm in depth, which stimulates new collagen growth beneath the epidermis "E".

Such treatments may beneficially utilize laser energy from each laser head, or energy at each of the wavelengths available from the Nd:YAG resonator. Without wishing to be bound by theory, it is believed that the utilization of alternating wavelengths, particularly rapidly alternating wavelengths, may provide significant clinical advantages. For example, an initial sub-pulse from the dye laser at 595 nm can be used to convert Oxy-hemoglobin in a vessel from its common chemical form into Met-hemoglobin, which provides much greater absorption at the 1064 nm wavelength of the Nd:YAG laser. Thus, treatment of such vessels can be effected at greatly reduced fluence, likely resulting in reduced side effects. Other benefits will be readily apparent to those of skill in the art, given the benefit of this disclosure. Further, treatments may utilize any of the combinations of sub-pulses described above that result from the use of active semiconductor switches. Suitable methods of treating skin utilizing a laser workstation in accordance with those described herein include the treatment of facial telangiectasias or vascular legions with the pulse dye laser at 595 nm; treatment of leg or facial veins with the pulse dye laser at 595 nm and/or the Nd:YAG laser at 1064 nm; treatment of active acne, acne scarring or other scars with the pulse dye laser at 595 nm in combination with the Nd:YAG laser at 1320 nm; and treatment of sun-damaged or wrinkled skin with the pulse dye laser at 595 nm and/or the Nd:YAG laser at 1320 nm. Other suitable uses for the laser workstation will be readily apparent to those skilled in the art, given the benefit of this disclosure.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A laser workstation comprising a first laser and a second laser, each laser having a laser medium and a laser pump chamber with an ionizable flashlamp for exciting the laser medium, an electronics drive system comprising:
   a controller adapted to enable selective activation of the first laser and second laser, said controller configured to selectively ionize each ionizable flashlamp, and
   an energy storage network which, subsequent to the selective ionization, provides energy simultaneously to each ionizable lamp, whereupon a selectively ionized lamp excites its associated laser medium to produce laser radiation.

2. The laser workstation of claim 1, further comprising a switch located between the energy storage network and the first laser pump chamber and the second laser pump chamber.

3. The laser workstation of claim 1, wherein each laser pump chamber is connected to the energy storage network by a high voltage trigger transformer which is operative to ionize its associated ionizable lamp.

4. The laser workstation of claim 1, wherein the first laser is a pulse dye laser.

5. The laser workstation of claim 4, wherein the pulse dye laser has an output of between about 575 nm and about 650 nm.

6. The laser workstation of claim 1, wherein the second laser is an Nd:YAG laser.

7. The laser workstation of claim 6, wherein the Nd:YAG laser comprises: an Nd:YAG lasing medium having a longitudinal axis; an output coupler located at a first end of the Nd:YAG lasing medium along the longitudinal axis of the Nd:YAG lasing medium; a first mirror located at a second end of the Nd:YAG lasing medium along the longitudinal axis of the Nd:YAG lasing medium, the first mirror being highly reflective at 1064 nm; a second mirror located between the first mirror and the second end of the Nd:YAG lasing medium along the longitudinal axis of the Nd:YAG lasing medium, the second mirror being highly reflective at 1320 nm and transparent at 1064 nm; and a beam block shutter movable from a first position along a longitudinal axis of the Nd:YAG lasing medium between the first and second mirrors along the longitudinal axis of the Nd:YAG lasing medium to a second position away from the longitudinal axis of the Nd:YAG lasing medium.

8. The laser workstation of claim 7, wherein the Nd:YAG lasing medium is a crystal rod.

9. The laser workstation of claim 7, wherein the second mirror is coated with a coating that is antireflective at 1064 nm.

10. The laser workstation of claim 1, further comprising a handpiece operatively connected to the first laser and second laser.

11. The laser workstation of claim 10, wherein the handpiece comprises a plurality of lenses operative to focus the laser radiation.

12. The laser workstation of claim 10, wherein the handpiece is connected to the first laser and second laser by an optical fiber.

13. The laser workstation of claim 9, wherein the handpiece is connected to the first laser and second laser by a wave guide.

14. The laser workstation of claim 1, wherein the energy storage network is operably connected to the first laser pump chamber by an active semiconductor switch and to the second laser pump chamber by an active semiconductor switch.

15. The laser workstation of claim 14, wherein the active semiconductor switches each are selected from the group consisting of an insulated gate bipolar transistor and a field effect transistor.

16. The laser workstation of claim 14, wherein the active semiconductor switch is an IGBT.

17. The laser workstation of claim 14, wherein the first laser device comprises a pulse dye laser.

18. The laser workstation of claim 14, wherein the first laser device comprises an Alexandrite laser.

19. The laser workstation of claim 18, wherein the Alexandrite laser is a variable pulse 755 nm Alexandrite laser.

20. The laser workstation of claim 14, wherein the second laser device comprises: a second lasing medium capable of lasing at a first wavelength and a second wavelength, the lasing medium having a longitudinal axis; an output coupler located at a first end of the lasing medium along the longitudinal axis of the lasing medium; a first mirror located at a second end of the lasing medium along the longitudinal axis of the lasing medium, the first mirror being highly reflective at the first wavelength; a second mirror located between the first mirror and the second end of the lasing medium along the longitudinal axis of the lasing medium, the second mirror being highly reflective at the second wavelength and transparent at the first wavelength; and a beam block shutter movable from a first position along the longitudinal axis of the lasing medium between the first and second mirrors along the longitudinal axis of the lasing medium to a second position away from the longitudinal axis of the lasing medium.

21. The laser workstation of claim 20, wherein the second laser device comprises an Nd:YAG laser.

22. The laser workstation of claim 21, wherein the first mirror is highly reflective at 1064 nm and the second mirror is highly reflective at 1320 nm and transparent at 1064 nm.

23. A method of treating a skin tissue comprising the steps of:

providing a laser device comprising a laser workstation comprising a first laser and a second laser, wherein the first laser and the second laser are driven by a single electronics drive system, said drive system comprising a single energy storage network connected to a first laser pump chamber with a first ionizable flashlamp and connected to a second laser pump chamber with a second ionizable flashlamp, wherein the first laser pump chamber is operative to excite a first laser medium to generate laser energy and the second laser pump chamber is operative to excite a second laser medium to generate laser energy;

treating an area of skin tissue by using the laser device to apply laser energy from the first laser at a first wavelength to the area of skin tissue and using the laser device to apply laser energy from the second laser at a second wavelength to the area of skin tissue, wherein the laser energy from the first laser is applied sequentially or simultaneously with energy from the second laser and wherein the laser energy from at least one of the lasers is applied in sub-pulses, wherein using the laser device to apply laser energy from the first laser comprises:

selectively ionizing said first flashlamp; and subsequently providing energy from said drive system simultaneously to each ionizable flashlamp whereupon the selectively ionized flashlamp excites its associated laser medium to generate laser energy, and wherein using the laser device to apply laser energy from the second laser comprises:

selectively ionizing said second flashlamp; and subsequently providing energy from said drive system simultaneously to each ionizable flashlamp whereupon the selectively ionized flashlamp excites its associated laser medium to generate laser energy.

24. The method of claim 23, wherein the laser energy from the first laser is at a different wavelength from the laser energy from the second laser.

25. The method of claim 24, wherein the first laser comprises a pulse dye laser and the second laser comprises: an Nd:YAG laser having a longitudinal axis; an output coupler located at a first end of the Nd:YAG laser along the longitudinal axis of the Nd:YAG laser; a first mirror located at a second end of the Nd:YAG laser along the longitudinal axis of the Nd:YAG laser, the first mirror being highly reflective at the 1064 nm; a second mirror located between the first mirror and the second end of the Nd:YAG laser along the longitudinal axis of the Nd:YAG laser, the second mirror being highly reflective at 1320 nm and transparent at 1064 nm; and a beam block shutter movable from a first position along a longitudinal axis of the Nd:YAG laser between the first and second mirrors along the longitudinal axis of the Nd:YAG laser to a second position away from the longitudinal axis of the Nd:YAG laser.

26. The method of claim 25, wherein the first wavelength is 595 nm and the second wavelength is 1064 nm.

27. The method of claim 25, wherein the skin tissue is leg or facial veins.

28. The method of claim 25, wherein the first wavelength is 595 nm and the second wavelength is 1320 nm.

29. The method of claim 28, wherein the skin tissue is acne, acne scarring, scarring, sun-damaged skin, or wrinkled skin.

30. The method of claim 23, wherein sub-pulses from the first laser are intercalated with sub-pulses from the second laser.

31. The method of claim 23, where a pulse train of sub-pulses from the first laser are followed by a sub-pulse from the second laser.

32. A method of treating a skin tissue comprising the steps of:

providing a laser device comprising a laser workstation comprising a first laser and a second laser, each laser having a laser medium and a laser pump chamber with an ionizable flashlamp for exciting the laser medium, an electronics drive system which selectively ionizes the flashlamps, and an energy storage network which, subsequent to the selective ionization, provides energy simultaneously to each ionizable lamp, whereupon a selectively ionized lamp excites its associated laser medium and treating the skin tissue by using the laser device to apply laser energy from the first laser to the skin tissue and using the laser device to apply laser energy from the second laser to the same skin tissue, wherein using the laser device to apply laser energy from the first laser comprises:

selectively ionizing said first flashlamp; and subsequently providing energy from said drive system simultaneously to each ionizable flashlamp whereupon the selectively ionized flashlamp excites its associated laser medium to generate laser energy, and wherein using the laser device to apply laser energy from the second laser comprises:

selectively ionizing said second flashlamp; and subsequently providing energy from said drive system simultaneously to each ionizable flashlamp whereupon the selectively ionized flashlamp excites its associated laser medium to generate laser energy.

33. The method of claim 32, wherein the first laser is a pulse dye laser and the second laser is a solid-state laser.

34. The method of claim 33, wherein the second laser is an Nd:YAG laser.

35. A method of treating a vascular lesion comprising the steps of:

providing a laser device comprising a laser workstation comprising a first laser and a second laser, wherein the first laser and the second laser are driven by a single electronics drive system comprising a single energy storage network connected to a first laser pump chamber and connected to a second laser pump chamber, wherein the first laser pump chamber is operative to excite a first laser medium and the second laser pump chamber is operative to excite a second laser medium; and treating a vascular lesion by using the laser device to apply laser energy at 595 nm from the first laser to the vascular lesion at an effective fluence to convert oxy-hemoglobin to met-hemoglobin, and then using the laser device to apply laser energy at 1064 nm from the second laser to the vascular lesion.

36. The method of claim 35, wherein the laser energy from at least one of the lasers is applied in sub-pulses.

37. The method of claim 36, wherein sub-pulses from the first laser are intercalated with sub-pulses from second laser.

38. The method of claim 36, where a pulse train of sub-pulses from the first laser are followed by a pulse train of sub-pulses from the second laser.

* * * * *